United States Patent
Shapiro et al.

(10) Patent No.: US 7,205,420 B2
(45) Date of Patent: Apr. 17, 2007

(54) EPIMERIZATION OF ANALOGS OF VITAMIN D

(75) Inventors: Evgeny Shapiro, Haifa (IL); Reinhard Effenberger, Haifa (IL); Asher Maymon, Petach Tikva (IL); Anchel Schwartz, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 131 days.

(21) Appl. No.: 10/459,073

(22) Filed: Jun. 11, 2003

(65) Prior Publication Data

US 2004/0054204 A1    Mar. 18, 2004

Related U.S. Application Data

(60) Provisional application No. 60/388,520, filed on Jun. 13, 2002.

(51) Int. Cl.
*C07C 401/00*    (2006.01)
*A61K 31/59*    (2006.01)

(52) U.S. Cl. ..................................... 552/653; 514/167
(58) Field of Classification Search ............... 435/68.1; 552/653; 514/167
See application file for complete search history.

(56) References Cited

U.S. PATENT DOCUMENTS

| 4,594,340 A | * | 6/1986 | Partridge et al. | ........... 514/167 |
| 4,866,048 A | * | 9/1989 | Calverley et al. | ........... 514/167 |
| 5,401,731 A | * | 3/1995 | Calverley et al. | ........... 514/167 |
| 5,665,716 A | * | 9/1997 | Kirsch et al. | ................ 514/167 |
| 6,531,459 B1 | * | 3/2003 | Steinmeyer et al. | ........ 514/167 |

FOREIGN PATENT DOCUMENTS

WO    WO 87/00834    2/1987

OTHER PUBLICATIONS

Barnett et al., AN 1941:4546 HCAPLUS, DN 35:4546, Sterol group. XLI. A new epimerization process, Journal of the Chemical Society, Abstracts (1940) 1390-3.*
Martin J. Calverley, "Synthesis of MC 903, A Biologically Active Vitamin D Metabolite Analogue," Tetrahedron, vol. 43, No. 20(1987) pp. 4609-4619.

* cited by examiner

*Primary Examiner*—Sabiha N. Qazi
(74) *Attorney, Agent, or Firm*—Kenyon & Kenyon LLP

(57) ABSTRACT

Provided is a method of general applicability of epimerizing a vitamin-D analog having an asymmetric allylic carbon atom at the C-24 position. The method is of particular utility in making calcipotriene.

24 Claims, No Drawings

EPIMERIZATION OF ANALOGS OF VITAMIN D

RELATED APPLICATIONS

The present application claims the benefit of the filing date of U.S. Provisional Patent Application 60/388,520, filed Jun. 13, 2002.

FIELD OF THE INVENTION

The present invention relates to analogs of vitamin D and derivatives thereof that have multiple asymmetric centers and to methods for epimerizing such vitamin D analogs and derivatives.

BACKGROUND OF THE INVENTION

In the preparation of Vitamin D analogs, in particluiar those having a structure analogous to I, a defined stereochemistry for the hydroxyl group at C-24 is necessary for full expression of the biological activity. As a specific example, the 24S epimer is desired for, for example, MC 903, (Structure I calcipotriene)

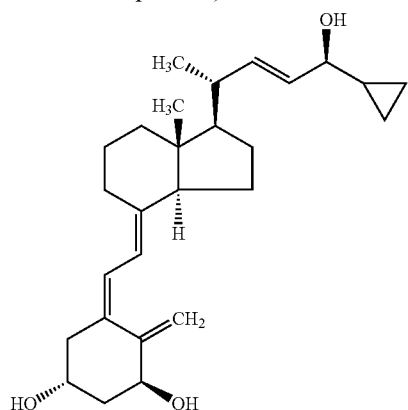

I

The standard process to make these vitamin D analogs is illustrated in Scheme I. The intermediate II (C-22 aldehyde vitamin D analogue) is reacted with a Wittig reagent to afford the unsaturated ketone III which is then reduced by, for example, sodium borohydride, to give IV as a mixture of C-24 epimers. See, e.g., Calverley *Tetrahedron* 4609–4619, 1987). The desired epimer, in this case the 24 S epimer is then separated by standard methods (for example, chromatography) and the undesired epimer, in this case the 24 R epimer, is discarded. Thus, waste is high and overall yield and process productivity are correspondingly low.

Scheme I

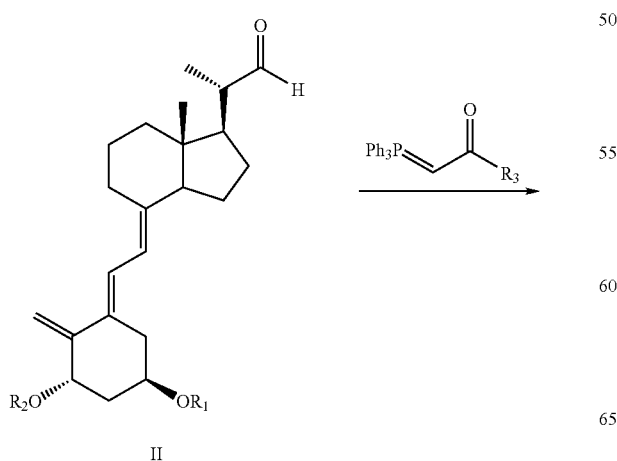

II

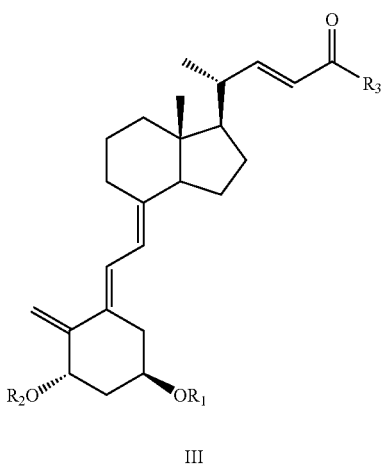

III

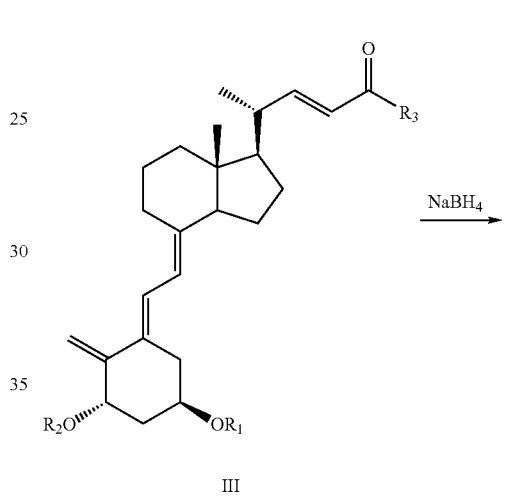

III

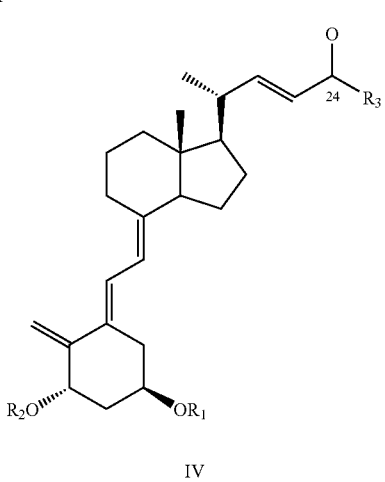

IV

We have discovered a method whereby the undesired epimer, here 24R, pure or contaminated with residual undesired 24S epimer, can be converted into a mixture enriched in the desired 24S epimer. This enriched mixture can be recycled to the separation step and thus the overall process productivity can be increased, waste reduced, and production costs lowered.

SUMMARY OF THE INVENTION

In one aspect, the present invention relates to a method of epimerizing a C-24 epimer of a vitamin D analogue having a hydroxyl group substituent on an asymmetric allylic carbon atom at the 24 position comprising the steps of esterifying the hydroxyl group on the asymmetric allylic carbon atom at the 24 position with an esterifying agent and contacting the ester with an epimerization-active solid.

In another aspect, the present invention relates to a method of epimerizing a C-24 epimer of a vitamin D analogue having a hydroxyl group substituent on an asymmetric allylic carbon atom at the 24 position comprising the steps of acetylating the hydroxyl group on the asymmetric allylic carbon atom at the 24 position with an acetylating agent and contacting the acetate ester so formed with an epimerization-active solid.

In another aspect, the present invention relates to a method of epimerizing a C-24 epimer of a vitamin D analogue having a hydroxyl group substituent on an asymmetric allylic carbon atom at the 24 position comprising the steps of acetylating the hydroxyl group on the asymmetric allylic carbon atom at the 24 position with an acetylating agent and contacting the acetate ester so formed with an epimerization-active solid selected from the group consisting of silica gel, aluminum oxide, florisil, and zeolite.

In another aspect, the present invention relates to a method of epimerizing a C-24 epimer of a vitamin D analogue having a hydroxyl group substituent on an asymmetric allylic carbon atom at the 24 position comprising the steps of acetylating the hydroxyl group on the asymmetric allylic carbon atom at the 24 position with an acetylating agent and contacting the acetate ester so formed with an epimerization-active solid selected from group consisting of silica gel, aluminum oxide, florisil, and zeolite, wherein the contacting is on a column packed with the epimerization-active solid.

In yet another aspect, the present invention relates to a method of epimerizing a C-24 epimer of a vitamin D analogue having a hydroxyl group substituent on an asymmetric allylic carbon atom at the 24 position comprising the steps of acetylating the hydroxyl group on the asymmetric allylic carbon atom at the 24 position with an acetylating agent and contacting the acetate ester so formed in a solvent selected from dichloromethane, hexane, heptane, toluene, ethyl acetate, and mixtures of these, with an epimerization-active solid selected from group consisting of silica gel, aluminum oxide, florisil, and zeolite.

In still another aspect, the present invention relates to a method of epimerizing a C-24 epimer of a vitamin D analogue having a hydroxyl group substituent on an asymmetric allylic carbon atom at the 24 position (a C-24 OH epimer) comprising the steps of acetylating the hydroxyl group on the asymmetric allylic carbon atom at the 24 position with an acetylating agent selected from acetic acid, acetyl chloride, and acetic anhydride, and <<contacting>> the acetate ester so formed with an epimerization-active solid.

In yet another aspect, the present invention relates to a method of epimerizing an epimeric C-24 ester of a vitamin D analogue having structure V or VIII.

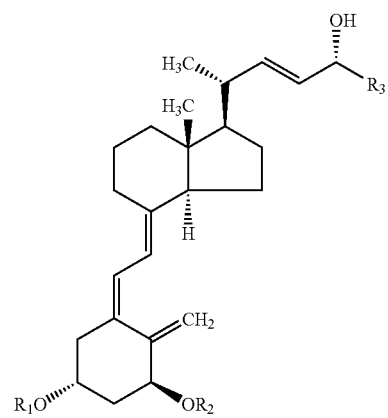

V

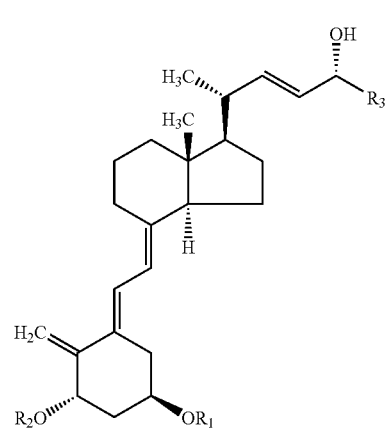

VIII wherein $R_1$ and $R_2$ are independently selected from hydrogen or a hydrogen protecting group and $R_3$ is a $C_1$–$C_6$ linear or branched alkyl or cycloalkyl group, comprising the step of contacting the C-24 epimeric ester with an epimerization-active solid.

In still another aspect, the present invention relates to a method of epimerizing a C-24 epimeric ester of a vitamin D analogue having structure V or VIII.

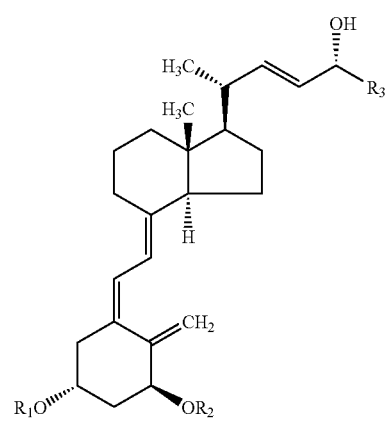

V

-continued

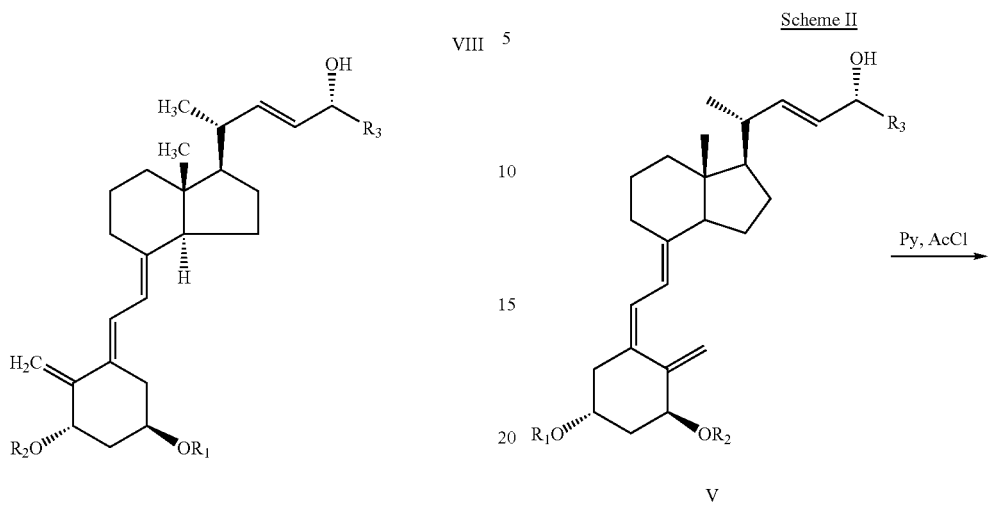

VIII wherein $R_1$ and $R_2$ are independently selected from hydrogen or a hydrogen protecting group and $R_3$ is a cycloalkyl group, comprising the step of contacting the C-24 epimeric ester with an epimerization-active solid.

DETAILED DESCRIPTION OF THE INVENTION

As used herein, ambient temperature refers to a temperature between about 18° C. and about 35° C., preferably about 25° C.

We herein disclose a novel process whereby the alcohols of general structures IV or VII are esterified with, for example, acetic anhydride or acetylchloride to the corresponding C-24 esters. The process is illustrated in Scheme II with the 24 R compounds-V and VIII. However, the process is equally applicable when the epimeric analog has the S configuration at C-24, or with mixtures epimeric anologs including both R and S configurations at C-24.

Esterification can be carried out by conventional means, or it can be carried out by enzyme-assisted esterification using, for example, vinyl acetate as disclosed in copending U.S. patent application Ser. No. 10/339,226, filed Jan. 9, 2003.

The esters are epimerized by contact with an epimerization-active solid, at ambient or elevated temperature, to afford, after hydrolysis, mixtures of the corresponding C-24 hydroxyl epimers that have a relatively higher concentration of the epimer originally absent or, in the case of mixtures, originally present in lesser amount.

We have found that, under certain conditions, an autohydrolysis can take place during the epimerization on the active solid. However, the empimerization can be carried-out without hydrolysis. The hydrolysis step can be carried out as a separate step using methods well known in the art. See Scheme III.

Scheme II

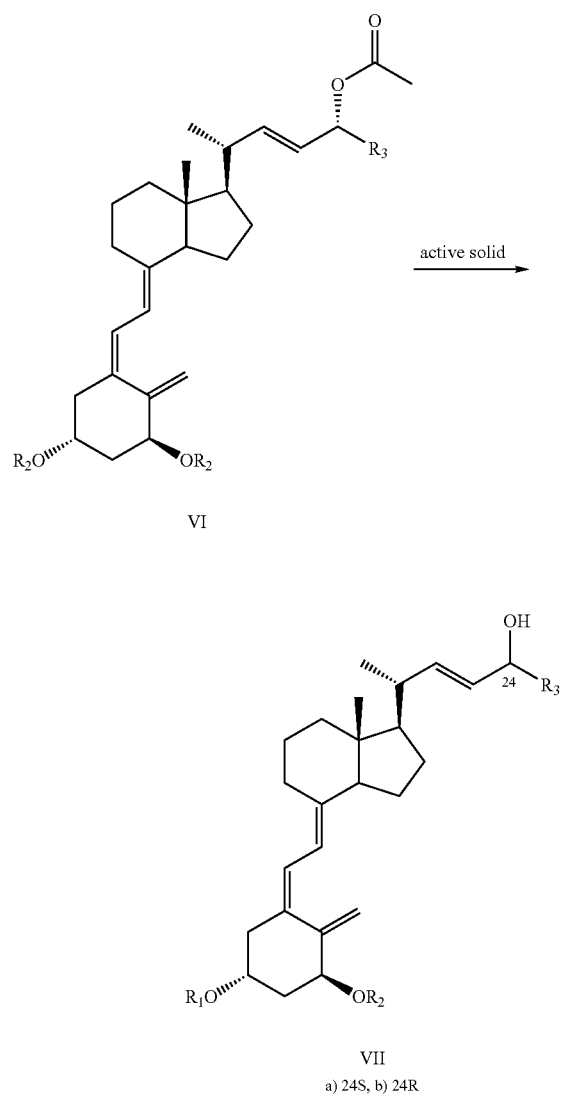

V

VI

VII
a) 24S, b) 24R

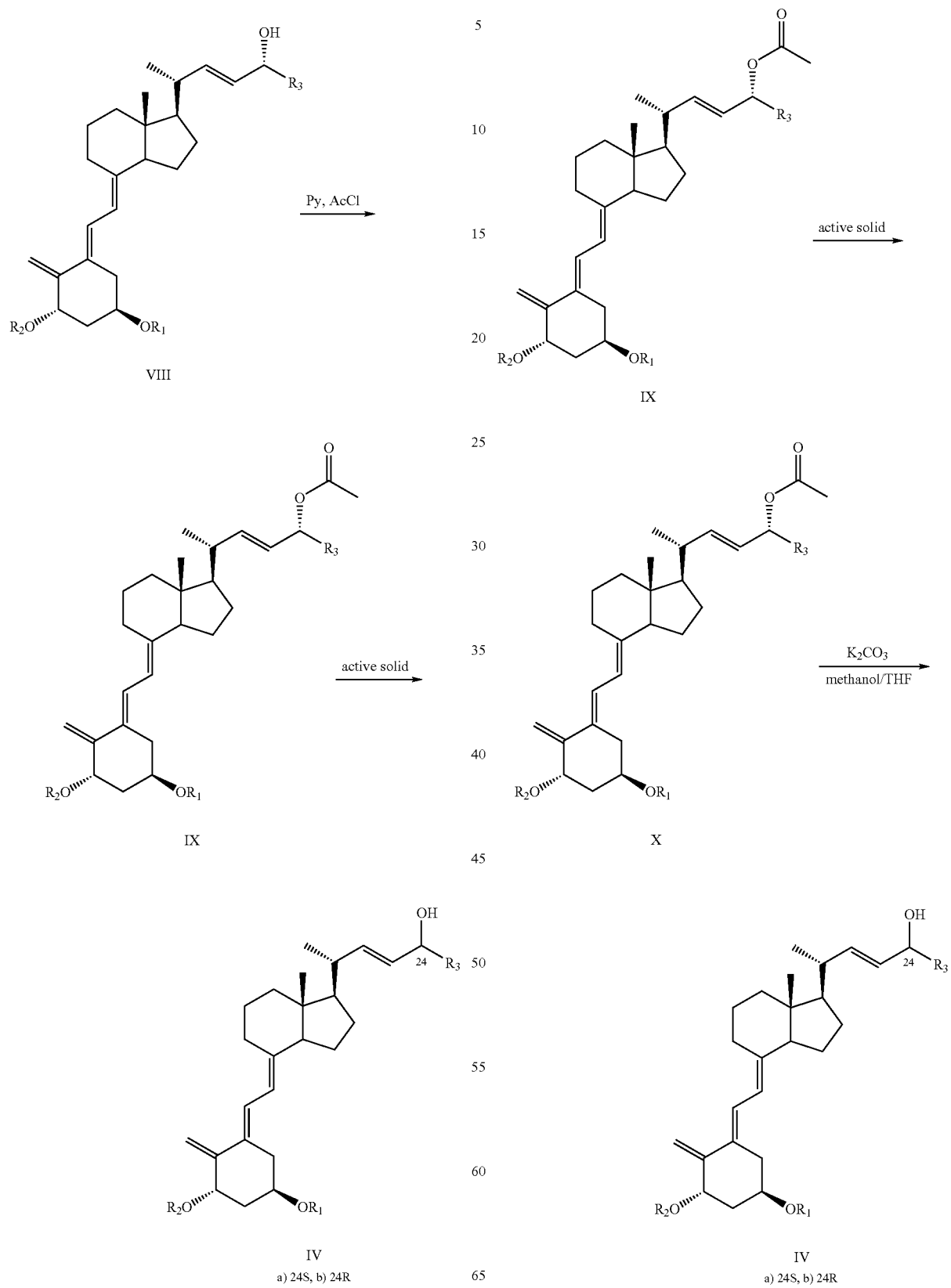

The present invention relates to epimers of vitamin D analogs. Epimers are diastereomers—that is configurational isomers that are not enantiomers—in compounds having more that one asymmetric carbon atom, wherein the configuration at only of the asymmetric centers differs between the two members of the epimeric pair. The process of converting one member of the epimeric pair to the other, by changing the stereochemistry at only one asymmetric center, can be referred to as epimerization.

The relative excess of one epimer over the other in a mixture of two epimers can be expressed in terms of diastereomeric excess, d.e., defined as $[E_1-E_2]$, where $E_i$ is the mole fraction of epimer i. Percent diastereomeric excess, % d.e., can be defined as $100 \cdot [E_1-E_2]$. Methods of determining d.e. and % d.e. are well known to one skilled in the stereochemistry of organic compounds.

The present invention provides a method for epimerizing a C-24 ester, especially an acetate, of a vitamin D analogue. Vitamin D analogs useful in the practice of the present invention are structurally related to cholecalciferol and, to the extent possible, the numbering system of the parent, cholesterol, is used. Vitamin D analogs useful in the practice of the present invention have an asymmetric allylic carbon atom that bears a free or derivatized hydroxyl group at C-24. Vitamin D analogs that are epimers, analogs, or structural or positional isomers, with respect to the exocyclic double bond on the A ring of a calciptotriene analogue, as exemplified by structures I, V, and VIII are particular objects of the present invention.

In the structures, $R_1$ and $R_2$ can be the same or different and are independently selected from hydrogen or hydroxyl protecting group. Preferred protecting groups are silyl protecting groups, for example trimethyl silyl, triethyl silyl, and, especially, t-butyl dimethyl silyl By the method of the present invention, a first C-24 epimer (either 24 S or 24 R) of a vitamin D analogue, alone or including some amount of a second epimer of a vitamin D analogue that has a configuration opposite to that of the first epimer at C-24, is converted to a mixture that is relatively enriched in the second epimer, relative to the strating mixture. That is, the diastereomeric excess of the starting epimer or mixture of epimers is decreased from its initial value.

The method of the present invention includes the step of contacting a C-24 ester of an epimer, or mixture of epimers, of a vitamin D analogue having an asymmetric allylic carbon atom at the 24 position with an epimerization-active solid. The ester can be obtained from any source. For example, the ester can be obtained by esterifying, using any esterification technique known in the art (including enzyme promoted esterification), a single epimer or a mixture of epimers of a vitamin D analogue having an OH group on the allylic carbon atom at position 24 for which it is desired to decrease the diastereometric excess. The ester is contacted in a suitable solvent. Suitable solvents include dichloromethane, hexane, heptane, toluene, ethyl acetate, and mixtures of these. When a solvent is used, hexane is a preferred solvent. The contacting can be at ambient temperature, or it can be at an elevated temperature, for example 35° C. or 40° C.

Epimerization-active solids are oxides of Group II, III, or IV elements. Examples of epimerization-active solids include silica gel, aluminum oxide, florisil, and zeolite, to mention just a few. The yield of the epimerization can be improved and the generation of byproducts reduced if a small amount of amine or inorganic base (e.g. $K_2CO_3$) are combined with the epimerization-active solid.

Preferably, the epimerization-active solid has a broad particle size distribution; for example from about 0.06 to about 0.20 mm or from about 0.04 to about 0.20 mm.

In the contacting step, epimerization of the C-24 ester occurs and the original percent diastereometric excess, which can be up to 100%, is decreased. That is, the relative amount of the epimer originally absent or present in a relatively smaller amount is increased. The contacting can be batchwise or it can be continuous. Batchwise contacting can be carried out in a suitable reactor provided with agitation, for example a flask or stirred tank reactor, or it can be carried out by loading the ester on a column, e.g. a chromatography column, packed with epimerization-active solid and eluted with a suitable solvent or mixture of solvents that can be any of the solvents discussed above.

In preferred embodiments, the solution of epimerized ester is separated from the epimerization-active solid. The epimerization-active solid is then washed at least once with a solvent. The solvent can be the same as the solvent in which the ester was contacted, or it can be different. Washing can be batchwise or it can be continuous (e.g. in a column). The washings are combined with the separated solution.

If desired, the mixed epimeric esters can be isolated, for example by removing any solvent(s) used, and then used for any purpose. If a mixture of epimeric alcohols is desired, the contacting step can be followed by a hydrolysis step in which the mixture of epimeric esters, now having a relatively larger amount of the epimer originally absent or present in a lesser amount, is hydrolyzed. If the epimeric C-24 alcohols are desired, the mixture of epimeric esters can be separated and the hydrolysis carried out on the desired epimer by any conventional method known in the art. For example, hydrolysis can be carried out in a suitable hydrolysis solvent using potassium carbonate. A mixture of methanol and tetrahydrofuran is an example of a suitable hydrolysis solvent.

Following hydrolysis, the epimeric C-24 alcohols can be isolated by, for example, removing the hydrolysis solvent using conventional techniques, for example with the aid of a rotary evaporator.

If desired, the hydrolysis step can be carried out in the presence of the epimerization-active solid without first isolating the ester. That is, epimerization and hydrolysis of the C-24 epimeric esters can be carried out in "one pot". Whether hydrolysis occurs in the presence of the epimerization-active solid is principally a function of the contacting time. The skilled artisan will recognize that this time may vary depending on, for example, the temperature of contacting, and the amount of water in the epimerization active solid. When the contacting is with silica gel and carried out at ambient temperature, a contacting time of about one hour is preferred. Longer contacting times can be tolerated without hydrolysis if alumina is the epimerization-active solid.

The esters and free alcohol are easily separated by chromatographic techniques and the hydrolysis can be monitored by chromatography, for example thin layer chromatigraphy (TLC).

Whether hydrolysis is carried out in situ (i.e. in "one-pot") or in a separate reaction step, the C-24 epimeric vitamin D analogs having a hydroxyl group on the carbon atom at the 24 position can be isolated and purified by any conventional means.

The present invention in several of its embodiments is illustrated in the following non-limiting examples.

EXAMPLE 1

One-pot Batch Process on Silica Gel in Hexane

To a round bottom 250 ml flask containing a solution of acetate IX ($R_3$=cyclopropyl, $R_2$=$R_3$=tert-butyldimethylsilyl (TBDMS), d.e. >97%,7.28 g) in hexane (180 ml), was added silica gel type 60 (0.043–0.060 mm, 71.93 g). The mixture was stirred slowly for 4 hr and then filtered. The silica gel was washed with ethyl acetate (300 ml), followed by a 10% solution of methanol in ethyl acetate. The filtrate and washings were combined and evaporated to dryness at 38° C./20 mbar to afford a crude product (6.55 g) containing 79.3% of a mixture of the epimeric alcohols IV ($R_3$=cyclopropyl, $R_2$=$R_1$=TBDMS) with d.e.=9%. The overall yield of IV was 81%.

Results for the batch epimerization of the acetate IX ($R_3$=cyclopropyl, $R_2R_3$=tert-butyldimethylsilyl), obtained as above but with shorter reaction time promoted by different types of silica gel in hexane, at various temperatures and silica gel/substrate ratios, are presented in Table 1.

TABLE 1

Results of the one-pot batch process promoted by silica gel in hexane

| No | Silica Gel (SG), Type, Particle Size Range (mm) | SG/substrate, g/g | SG/Hex, g/ml | Temp, °C. | Time, hr. | Purity, % | DE, % | Yield, % |
|---|---|---|---|---|---|---|---|---|
| 39 | 40, 0.063–0.200 | 10.4 | 0.5 | 20 | 6 | 71 | 6 | 64 |
| 40 | 40, 0.063–0.200 | 4.7 | 0.27 | 20 | 23 | 57 | 4 | 51 |
| 41 | 60, 0.040–0.063 | 9.8 | 0.53 | 20 | 6 | 78.2 | 10 | 79 |
| 42 | 60, 0.040–0.063 | 4.3 | 0.24 | 20 | 23 | 59.2 | 3 | 55 |
| 43 | 40, 0.063–0.200 | 4.9 | 0.27 | 40 | 3.5 | 53.3 | 2 | 47 |
| 44 | 60, 0.040–0.063 | 4.3 | 0.23 | 40 | 3.5 | 54 | 3 | 53 |
| 45 | 40, 0.063–0.200 | 17 | 0.88 | 20 | 2.5 | 79.2 | 6 | 76 |
| 46 | 60, 0.040–0.063 | 13.2 | 0.58 | 20 | 3.0 | 81.3 | 9 | 80 |
| 47 | 40, 0.063–0.200 | 16.4 | 0.71 | 0–5 | 25 | 78 | 5 | 82 |
| 48 | 60, 0.040–0.063 | 13.7 | 0.58 | 0–5 | 26 | 73 | 9 | 70 |
| 49 | 60, 0.040–0.063 | 14.5 | 0.57 | 20 | 3.5 | 81.5 | 9 | 79 |
| 50 | 60, 0.040–0.063 | 9.9 | 0.40 | 20 | 4 | 79 | 9 | 81 |
| 53 | 60, 0.040–0.063 | 10.1 | 0.59 | 20 | 3.5 | 73.6 | 4.6 | 67 |
| 57 | 60, extra pure, 0.063–0.200 | 9.9 | 0.53 | 20 | 25 | 52.3 | 10 | 49 |
| 58 | 100, 0.063–0.200 | 9.9 | 0.43 | 20 | 24 | 66.3 | 16 | 56 |

Legend:
SG/Hex - Silica Gel/hexane ratio
Purity - total content of alcohols IV (a and b, $R_3$ = cyclopropyl, $R_2$ = $R_3$ = TBDMS) in isolated product
DE - diastereomeric excess

EXAMPLE 2

2-Step Batch Process on Silica Gel Following Hydrolysis with $K_2CO_3$

To a round bottom 50 ml flask containing a solution of acetate IX ($R_3$=cyclopropyl, $R_2$=$R_3$=tert-butyldimethylsilyl, TBDMS, d.e. >97%1.02 g) in hexane (20 ml), was added silica gel grade 40 (0.063–0.200 mm, 4.61 g). After stirring for about an hour, the contents of the flask were filtered and the residual silica gel was washed with ethyl acetate (50 ml). The filtrate and washing were combined and evaporated to dryness at 38° C./20 mbar to afford a crude product (0.935 g) containing 50.1% of a mixture of acetates X ($R_3$=cyclopropyl, $R_2$=$R_3$=tert-butyldimethylsilyl, TBDMS) with d.e. 7.4%. These were dissolved in Methanol/THF (2.5 ml:2.5 ml), anhydrous potassium carbonate (0.61 g) was added and the mixture was stirred overnight. The solvent was removed under reduced pressure and the residue was extracted with hexane (3×30 ml). The extracts were combined and evaporated to afford 0.873 g of a crude product, containing 76.2% of a mixture of alcohols IV ($R_3$=cyclopropyl, $R_2$=$R_3$=tert-butyldimethylsilyl, TBDMS) with d.e. 7%. in 72% yield.

EXAMPLE 3

2-Step Batch Process on Alumimum Oxide

To a round bottom 100 ml flask containing a solution of acetate IX ($R_3$=cyclopropyl, $R_2$=$R_3$=TBDMS, d.e. >97% 2.2 g) in hexane (44 ml), was added basic aluminum oxide (90, 0.063–0.200 23.1 g). After stirring over 6 hours the content was filtered and the residual alumina was then washed with ethyl acetate (80 ml). The filtrate and washing were combined and evaporated to dryness at 38° C./20 mbar to afford a crude product (1.97 g) containing 59% of a mixture of acetates X ($R_3$=cyclopropyl, $R_2$=$R_3$=tert-butyldimethylsilyl, TBDMS). The residue was dissolved in Methanol/dichloromethane (3.5 ml:2.5 ml), anhydrous potassium carbonate (1.3 g) was added and the mixture was stirred overnight. The solvent was removed under reduced pressure and the residue was extracted with hexane (2×40 ml). The extracts were combined and evaporated to afford 1.68 g of a crude product, containing 93% of a mixture of alcohols IV with d.e. 69%. Yield 98%.

EXAMPLE 4

The general procedure outlined above for the two-step batchwise process was employed in each of the experimental runs discussed in the table below.

Results for the two-step batch epimerization of acetates IX ($R_3$=cyclopropyl, $R_2$=$R_3$=TBDMS) promoted by different types of silica gels in various solvents, under various silica gel: substrate ratios at 20° C., are presented in Table 2. Results of the two-step batch epimerization of acetate IX $R_3$=cyclopropyl, $R_2$=$R_3$=tert-butyldimethylsilyl, TBDMS) promoted by different types of active solids are presented in Table 3.

TABLE 2

Results of the 2-step batch process promoted by silica gel in various solvents (at 20° C.)

| No | Silica Gel (SG), Type, Particle Size Range (mm) | SG/Sub, g/g | Solvent | Co-solvent, (% v/v) | SG/S, g/ml | Time, h | SH | YH, % | Purity, % | DE, % | Yield, % |
|---|---|---|---|---|---|---|---|---|---|---|---|
| 7  | 60, 0.063–0.200 | 6.9  | DCM    | —         | 0.37 | 1.5  | MeOH/THF | ND | 61   | −5  | 55   |
| 9  | 40, 0.063–0.200 | 9.5  | DCM    | —         | 0.49 | 2    | MeOH/THF | ND | 71   | −2  | 68   |
| 11 | 60, 0.063–0.200 | 2.6  | DCM    | —         | 0.15 | 0.75 | MeOH/THF | 17 | 89   | 50  | 89   |
| 12 | 40, 0.063–0.200 | 4.1  | DCM    | —         | 0.18 | 0.92 | MeOH/THF | 28 | 82   | 7   | 81   |
| 13 | 40, 0.2–0.5     | 3.2  | DCM    | —         | 0.18 | 0.83 | MeOH/THF | 17 | 89   | 44  | 86   |
| 14 | 60, 0.04–0.063  | 1.5  | DCM    | —         | 0.08 | 1    | MeOH/THF | 14 | 89.6 | 56  | 102  |
| 15 | 40, 0.063–0.200 | 2.1  | DCM    | —         | 0.11 | 1    | MeOH/THF | 18 | 84.8 | 25  | 96   |
| 16 | 60, 0.04–0.063  | 0.7  | DCM    | —         | 0.04 | 1    | MeOH/THF | 11 | 90.5 | 67  | 92   |
| 17 | 40, 0.063–0.200 | 1.05 | DCM    | —         | 0.05 | 1    | MeOH/THF | 14 | 87.6 | 43  | 105  |
| 18 | 40, 0.063–0.200 | 1.02 | DCM    | —         | 0.06 | 1    | MeOH/THF | 17 | 86.3 | 22  | 83   |
| 19 | 40, 0.063–0.200 | 0.79 | DCM    | —         | 0.04 | 1    | MeOH/THF | 18 | 88.6 | 40  | 95   |
| 21 | 40, 0.063–0.200 | 6.02 | DCM    | —         | 0.31 | 1    | MeOH/THF | 30 | 80.2 | 2   | 72   |
| 26 | 40, 0.063–0.200 | 4.6  | DCM    | MeOH (1)  | 0.20 | 1    | MeOH/DCM | 10 | 73.6 | 50  | 72   |
| 27 | 40, 0.063–0.200 | 4.5  | DCM    | TEA (1)   | 0.23 | 1    | MeOH/DCM | 13 | 92   | 69  | 85   |
| 28 | 40, 0.063–0.200 | 4.5  | Hexane | —         | 0.23 | 1    | MeOH/DCM | 50 | 76.2 | 7   | 72   |
| 29 | 40, 0.063–0.200 | 4.6  | Hexane | —         | 0.22 | 1    | MeOH/DCM | 68 | 74   | 5   | 70   |
| 30 | 60, 0.063–0.200 | 3.5  | Hexane | —         | 0.19 | 1    | MeOH/DCM | 44 | 83.6 | 16  | 80   |
| 31 | 60, 0.063–0.200 | 3.3  | Hexane | —         | 0.18 | 2    | MeOH/DCM | 56 | 79.2 | 8   | 70   |
| 34 | 40, 0.063–0.200 | 9.7  | Hexane | —         | 0.57 | 1    | MeOH/DCM | 63 | 82.8 | 6   | 76   |
| 35 | 40, 0.063–0.200 | 9.3  | Hexane | —         | 0.56 | 2    | MeOH/DCM | 64 | 79.3 | 8.2 | 61   |
| 36 | 60, 0.040–0.063 | 9.0  | Hexane | —         | 0.53 | 1    | MeOH/DCM | 63 | 82.8 | 6   | 76   |
| 37 | 60, 0.040–0.063 | 8.7  | Hexane | —         | 0.50 | 2    | MeOH/DCM | 71 | 79.5 | 9   | 72   |
| 38 | 40, 0.063–0.200 | 3.7  | Hexane | Water, 0.5| 0.22 | 1    | MeOH/DCM | 50 | 77.7 | 6   | 69   |
| 54 | 60, 0.040–0.063 | 13.4 | Toluene| —         | 0.48 | 26   | Toluene  | 51 | 51.6 | −10 | 51.6 |
| 55 | 40, 0.063–0.200 | 14.7 | Toluene| —         | 0.50 | 26   | Toluene  | 51 | 59.4 | −9  | 51   |
| 56 | 60, 0.040–0.063 | 10.2 | TBME   | —         | 0.49 | 72   | MeOH/DCM | 51 | 83.9 | 94  | 37   |

Legend:
SG/Sub - silica gel/substrate ratio.
SG/S - silica gel/solvent ratio.
SH - solvent for hydrolysis.
YH - extent of hydrolysis of acetate X ($R_3$ = cyclopropyl, $R_1$ = $R_2$ = TBDMS) during epimerization.
Purity - total content of alcohols IV ($R_3$ = cyclopropyl, $R_1$ = $R_2$ = TBDMS) in final product.
DE - diastereomeric excess;
Yield - overall yield of alcohols IV and VII ($R_3$ = cyclopropyl, $R_1$ = $R_2$ = TBDMS) after epimerization-hydrolysis;
Solvents:
DCM - dichloromethane,
TBME - tert-butyl methyl ether

TABLE 3

Results of the 2-step batch process promoted by different active solids in various solvents at 20° C.

| No | Active solid, Particle Size Range (mm) | Solid/Sub-ratio, g/g | Solvent | Sol/S, g/ml | Time, h | CH | YH, % | Purity, % | DE, % | Yield, % | Notes |
|---|---|---|---|---|---|---|---|---|---|---|---|
| 32 | Celite 521 | 4.1 | DCM | 0.20 | 1 | C | 0 | 94.9 | 96 | 100 | |
| 33 | Molecular sieves, 4A | 3.9 | DCM | 0.20 | 1 | C | 0 | 94.1 | 92 | 73 | |
| 51 | Aluminum oxide basic 90, 0.063–0.200 mm | 10.5 | Hexane | 0.52 | 6 | D | 23 | 91 | 70 | 90 | |
| 52 | Aluminum oxide neutral 90, 0.063–0.200 mm | 10.1 | Hexane | 0.51 | 6 | D | 38 | 93 | 69 | 98 | |
| 59 | Florisil, 60–100 mesh | 9.7 | Hexane | 0.32 | 24 | D | ND | ND | ND | ND | Non-selective decomposition |
| 60 | Florisil, activated at 675° C., 60–100 mesh | 9.7 | Hexane | 0.32 | 24 | C | 4 | 81.5 | 62 | 79 | |

Legend:
Solid/Sub - active solid/substrate ratio
Sol/S - active solid/solvent ratio
CH - conditions for hydrolysis:
C - $K_2CO_3$ in methanol/DCM,
D - autohydrolysis on the active solid
YH - extent of hydrolysis of acetate X ($R_3$ = cyclopropyl, $R_1$ = $R_2$ = TBDMS) during epimerization
Purity - total content of alcohols IV and VII ($R_3$ = cyclopropyl, $R_1$ = $R_2$ = TBDMS) in final product
DE - diastereomeric excess
Yield - overall yield of alcohols IV and VII ($R_3$ = cyclopropyl, $R_1$ = $R_2$ = TBDMS) after epimerization-hydrolysis
DCM dichloromethane

EXAMPLE 5

Epimerization in a Column Packed with Silica Gel Followed by Hydrolysis with $K_2CO_3$ A solution of acetate IX ($R_3$=cyclopropyl, $R_1$=$R_2$=TBDMS, 1.032 g, d.e. >97%) in dichloromethane (DCM) (2 ml) was placed on the top of a column (ID 18 mm) packed with 30 g of silica gel grade 60 (0.040–0.063 mm). The column was eluted with DCM (50 ml), followed by a mixture of DCM:EA:water (40:10:0.05 ml). The eluates were combined and evaporated to afford 1.058 g of a crude product. This was dissolved in tetrahydrofuran (5 ml) and anhydrous potassium carbonate (0.660 g) was added, followed by methanol (10 ml), and the mixture was stirred overnight at 20–22° C. The solvent was removed under reduced pressure and the residue was extracted with hexane (3×30 ml). The extracts were combined, washed with water (~10 ml) and evaporated to afford 1.057 g of a crude product containing a mixture of alcohols IV ($R_3$=cyclopropyl, $R_1$=$R_2$=TBDMS) d.e. 78%. Yield ~100%.

EXAMPLE 6

The general column method discussed above was repeated with different silica gels as the epimerization-active solid. The results are given below.

Results of the epimerization of esters (IX) ($R_3$=cyclopropyl, $R_1$=$R_2$=TBDMS) at 20° C. in a column packed with various silica gels of different granule size, using various solvents for the elution, are presented in Table 4. Note that the ester in No. 65 is of propionate.

TABLE 4

Results of the epimerization of esters IX ($R_3$ = cyclopropyl, $R_1$ = $R_2$ = TBDMS) on a silica gel column, followed by hydrolysis with $K_2CO_3$ in MeOH/THF

| No | Ester | Type SG, Granule size, mm | SG/Sub, g/g | Eluent | Purity, % | DE, % | Yield, % |
|---|---|---|---|---|---|---|---|
| 3 | Ac | 40, 0.2–0.5 | 7.5 | DCM, EA | 93 | 81 | Quant. |
| 5 | Ac | 40, 0.063–0.200 | 7.3 | DCM, EA | 91 | 69 | Quant. |
| 65 | PrCO | 60, 0.063–0.200 | 7.5 | Hexane, EA | 78 | 10 | 61 |
| 66 | Ac | 60, 0.063–0.200 | 15 | Hexane, EA + 2.5% AcOH | 91 | 93 | 87 |
| 67 | Ac | 60, 0.063–0.200 | 15 | DCM | 86 | 49 | 85 |

EXAMPLE 7

Epimerization of Acetate VI ($R_3$=cyclopropyl, $R_1$=$R_2$=TBDMS)

To a round bottom 25 ml flask containing mixture of VI and IV a (0.37 g 60:40, $R_3$=cyclopropyl, $R_1$=$R_2$=TBDMS) dissolved in hexane (5 ml), was added silica gel 60 (0.040–0.063 mm, 2.31 g). The mixture was stirred slowly for 1.5 h then filtered. The silica gel was washed with ethyl acetate (50 ml). The filtrate and washings were combined and evaporated to dryness at 38° C./20 mbar to afford a crude product (0.3 g), containing a mixture of diastereomeric alcohols IV enriched with alcohol IV a ($R_3$=cyclopropyl, $R_1$=$R_2$=TBDMS), d.e. 18.4%

EXAMPLE 8

Epimerization of Acetate VI ($R_3$=cyclopropyl, $R_1$=$R_2$=H)

To a round bottom 50 ml flask containing a solution of the acetate VI (0.44 g, $R_3$=cyclopropyl, $R_1$=$R_2$=H, d.e.>98%) in a mixture of DCM (5 ml) and hexane (5 ml), was added silica gel grade 60 (0.040–0.063 mm, 4.86 g). The mixture was stirred slowly for 24 h. HPLC analysis showed that the reaction mixture contained a mixture of alcohols VII ($R_3$=cyclopropyl, $R_1$=$R_2$=H) d.e.=20%.

EXAMPLE 9

Epimerization of Alcohol VIII ($R_3$=cyclopropyl, $R_1$=$R_2$=TBDMS) In Situ Via Enzyme-promoted Acylation with Vinyl Acetate To a round bottom 50 ml flask containing a solution of alcohol VIII ($R_3$=cyclopropyl, $R_1$=$R_2$=TBDMS, 0.502 g, 0.69 mmol, d.e.>98%) in hexane (10 ml), were added lipase from *Pseudomonas* sp. (0.15 g,) and vinyl acetate (0.29 ml, 3.12 mmol). The mixture was stirred at room temperature for 3 h. The mixture was diluted with hexane (20 ml) then anhydrous potassium carbonate (1.69 g, 16.7 mmol), followed by silica gel 60 (0.043–0.060 mm, 4.96 g) were added. The mixture was stirred for 2 days and filtered. The cake was washed with ethyl acetate (2×25 ml) and evaporated under reduced pressure to afford 0.486 g of crude product containing 76% of a racemic mixture of the alcohols IV ($R_3$=cyclopropyl, $R_1$=$R_2$=TBDMS), d.e. 4.5%. Yield 83%.

EXAMPLE 10

Epimerization on Silica Gel Column of Alcohol VIII ($R_3$=cyclopropyl, $R_1$=$R_2$=TBDMS) In Situ Via the Mitsunobu Reaction To a round bottom 10 ml flask containing a solution of alcohol VIII ($R_3$=cyclopropyl, $R_1$=$R_2$=TBDMS, 0.502 g, 0.7 mmol, d.e. >98%), triphenylphosphine (0.378 g, 1.4 mmol, and p-nitrobenzoic acid (0.239 g, 1.4 mmol) in anhydrous tetrahydrofuran (6 ml), was added a solution of diisopropyl azodicarboxylate (0.30 g, 1.4 mmol) in anhydrous tetrahydrofuran (4 ml). The mixture was heated to 60° C. and stirred for 4.5 h, then extracted with hot hexane (50° C., 3×10 ml). The extracts were combined and evaporated under reduced pressure to afford 1.066 g of a crude product containing the nitrobenzoyl ester at C-24 with d.e. 98%. This was placed on top of a column (ID18 mm) packed with 20 cc of silica gel 60 (0.040–0.063 mm). The column was eluted with gradient of hexane-EA to afford 0.263 g, containing ~70% of racemic mixture of the alcohols IV ($R_3$=cyclopropyl, $R_1$=$R_2$=TBDMS), d.e. 5%. Yield 37%.

EXAMPLE 11

Epimerization of Alcohol VIII ($R_3$=cyclopropyl, $R_1$=$R_2$=TBDMS) Using Silica Gel Treated with Triethyl Amine To a round bottom 1000 ml flask containing a solution of acetate IX ($R_3$=cyclopropyl, $R_2$=$R_3$=TBDMS, d.e. >97% 20 g) in hexane (400 ml) and triethylamine (2 ml, 14.4 mmol), was added silica gel grade 60 (0.043–0.060 mm, 200 g). The mixture was stirred slowly for 7 h and then filtered. The silica gel was washed with ethyl acetate (2×200 ml). The filtrate and washings were combined and evaporated to dryness at 38° C./20 mbar to afford a crude product (20.6 g) containing 80.3% of a mixture of the epimeric alcohols IV ($R_3$=cyclopropyl, $R_2$=$R_1$=TBDMS) with d.e.=0.4%. The overall yield of IV was 85%.

EXAMPLE 12

Preparation Calcipotriene (I)

A solution of alcohol IVa =VIII ($R_1$=$R_2$=tert-butyldimethylsilyl, $R_3$=cycloprpyl) (15.3 g, 24 mmol), 9-acetylanthracene (1.6 g, 7.2 mmol), and triethylamine 350 µL in toluene (1200 ml) contained in a photochemical reactor and cooled to 5–8° C. Irradiated with light from a high pressure ultra-violet lamp to completion (~45 min.) and reaction mixture was transferred to evaporation together with 2×100 ml toluene from rinsing the reactor. Drying under high vacuum gave crude alcohol VII a 15.3 g.

The alcohol VIIa was dissolved in THF (450 ml) and tetrabutylammonium fluoride (45 ml, 45 mmol) was added. The mixture was heated at 40° C. for 2 hours under atmosphere of nitrogen and evaporated to dryness. The residue was dissolved in ethyl acetate (1200 ml) and washed with 2% sodium bicarbonate solution (2×150 ml) following with 250 ml brine. After drying with $Na_2SO_4$ the solution was evaporated to dryness. The residue was chromatographed on silica gel (1200 g) eluted with mixture of ethyl acetate in hexane. Collection of the appropriate fractions (checked by TLC) and evaporation gave 7 g of a foam.

Three grams of the product were crystallized from methyl formate to give 2.6 g Calcipotriene structure I.

EXAMPLE 13

Enzymatic Esterification

To a stirred solution of C-24 epimeric alcohol mixture of structure IV, $R_1$=$R_2$=tert butyldimethylsilyl and $R_3$=cyclopropyl, (20 gr, 31.2 mmol) and vinyl acetate (5.8 ml, 62.4 mmol) in hexane (60 ml) was added 0.56 gr Alcaligenes sp. Lipase. The mixture was stirred for 3 hours at 25±3° C. after which time the HPLC analysis showed essentially complete conversion of epimer C-24 (R) to the acetate. The remaining nonesterified C-24 (S) alcohol was >99% diastereomeric excess (by HPLC). The solution was filtered and concentrated to dryness. The residue was chromatographed on pre-treated silica gel with 5% ethyl acetate in hexane then with ethyl acetate to give C-24 acetate compound IX (11 gr) and C-24 alcohol having the opposite configuration at C-24 (7.4 gr).

The purity profile of the product was as follows.

|  | Purity profile | | | Instrument and method |
|---|---|---|---|---|
| Compound | X | Alcohol | VIII | Merck-Hitachi |
| IV | 93.1 | 0.2 | — | Model: L-6200A intelligent |
| Alcohol | 0.5 | 89.0 | 1.6 | pump. Mobile phase : 0.5% amyl alcohol in hexane |

EXAMPLE 14

Enzymatic Esterification

To a vial containing 100 mg (0.16 mmol) of mixed C-24 epimers of C-24 alcohol of structure IV, with $R_1$=$R_2$=tert-butyldimethylsilyl and $R_3$=cyclopropyl, (65:35 isomer ratio), 0.044 ml (0.47 mmol) vinyl acetate and 1.5 ml diisopropyl ether, 10 mg of *Alcaligenes* sp. lipase was added. The mixture was stirred at room temperature for 2 hours after which time the HPLC analysis showed the presence of 65% compound IX and 35% of the alocihol having opposite configuration at C-24.

What is claimed is:

1. A method of epimerizing a C-24 epimer of a vitamin D analog having a hydroxyl substituent on an asymmetric allylic carbon at the 24 position comprising the steps of:
    a) esterifying the hydroxyl group on the asymmetric allylic carbon atom at the 24 position with an esterifying agent,
    b) contacting>> a solution of the ester in a solvent with an epimerization-active solid, whereby the ester is epimerized, and
    c) hydrolyzing the epimerized ester to obtain a mixture of C-24 epimers having a hydroxyl substituent on the asymmetric allylic carbon at position 24.

2. The method of claim 1 wherein the ester is an acetate.

3. The method of claim 2 wherein the hydroxyl group is esterified with an esterifying agent selected from acetic acid, acetyl chloride, and acetic anhydride.

4. The method of claim 2 wherein the acetate ester of the vitamin D analog can be represented by either of structure VI or IX

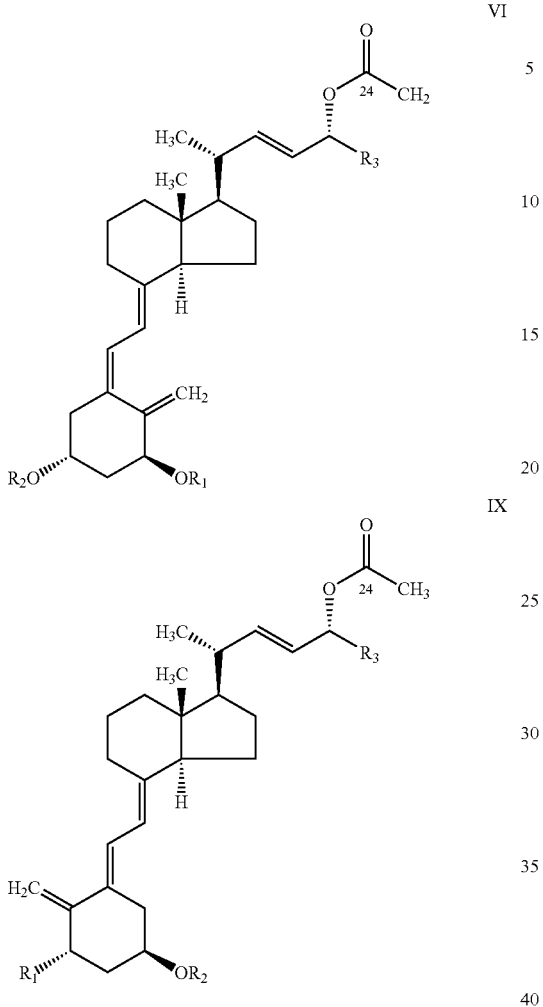

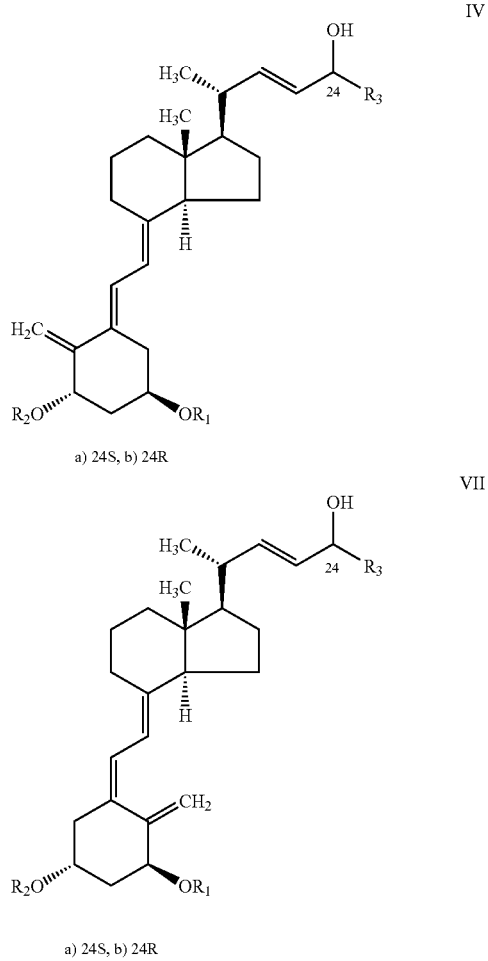

a) 24S, b) 24R wherein $R_1$ and $R_2$ can be the same or different and are selected from hydrogen and a silyl hydroxyl protecting group and $R_3$ is a $C_1$–$C_6$ alkyl or cycloalkyl group.

5. The method of claim 1 wherein the epimerization active solid is selected from the group consisting of silica gel, aluminum oxide, florisil, and zeolite.

6. The method of claim 5 wherein an amine or an inorganic base is combined with the epimerization-active solid.

7. The method of claim 6 wherein the inorganic base is potassium carbonate.

8. The method of claim 1 further comprising, after the contacting step, the steps of:
1) separating the solution of epimerized ester from the epimerization-active solid,
2) washing, at least once, the separated epimerization-active solid with a solvent that can be the same or different from the solvent in which the ester to be epimerized was contacted,
3) combining the washings with the separated solution of epimerized ester, and
4) removing solvent to obtain the epimerized ester.

9. The method of claim 1 wherein the contacting is at a temperature of about 35° C.

10. A method of decreasing the diastereometric excess of a starting mixture of epimers of a vitamin D analog, which analog is represented by one or the other of structures IV or VII a) 24S, b) 24R a) 24S, b) 24R wherein $R_1$ and $R_2$ can be the same or different and are selected from hydrogen and silyl hydroxyl protecting group and $R_3$ is a $C_1$–$C_6$ alkyl or cycloalkyl group, comprising the steps of:
a) acetylating the hydroxyl group at the 24 position with an acetylating agent to form the corresponding acetate ester,
b) providing a solution of the acetylated vitamin D analog in a solvent selected from hexane, heptane, toluene, benzene, dichloromethane, ethyl acetate, and mixtures of these,
c) contacting the solution with an epimerization-active solid whereby the ester is epimerized to obtain a solution of epimers of esterified vitamin D analog having a diastereometric excess that is less than that of the starting mixture of epimers, and
d) hydrolyzing the epimerized esters to obtain a mixture of epimers of vitamin D analog having a diastereometric excess that is less than that of the starting mixture.

11. The method of claim 10 wherein $R_3$ is cyclopropyl.

12. The method of claim 10 wherein $R_1$ and $R_2$ are t-butyl dimethylsilyl.

13. The method of claim 10 wherein the acetylating agent is selected from acetyl chloride and acetic anhydride.

14. The method of claim 10 wherein the acetylating is by enzyme-assisted acetylation with vinyl acetate.

15. The method of claim 10 wherein the epimerization-active solid is selected from the group consisting of silica gel, aluminum oxide, florisil, and zeolite.

16. The method of claim 15 wherein the epimerization-active solid is combined with an amine or an inorganic base.

17. The method of claim 16 wherein the inorganic base is potassium carbonate.

18. A method for making mixed epimers of a vitamin D analog having a hydroxyl substituent on an asymmetric allylic carbon atom at the C-24 position, starting from an individual C-24 OH epimer or a mixture of C-24 OH epimers having an initial diastereometric excess, comprising the steps of:
   a) esterifying the hydroxyl group on the asymmetric allylic carbon atom at the C-24 position of the epimer or epimers with an esterifying agent,
   b) contacting a solution of the ester in a solvent with an epimerization-active solid, whereby the ester is epimerized, and
   c) hydrolyzing the epimerized ester to obtain a mixture of C-24 epimers having a hydroxyl substituent on the asymmetric allylic carbon at position 24, wherein the diastereometric excess of the mixture is less than the initial diastereometric excess.

19. The method of claim 18 wherein the epimerization-active solid is combined with an amine or an inorganic base.

20. The method of claim 19 wherein the inorganic base is potassium carbonate.

21. The method of claim 18 wherein the contacting is at a temperature of about 35° C.

22. The method of claim 18 wherein the ester is in solution in a solvent selected from hexane, heptane, toluene, benzene, dihloromethane, ethyl acetate, and mixtures of these.

23. The method of claim 18 further comprising, after the contacting step, (b), the steps of:
   1) separating the solution of epimerized ester from the epimerization-active solid,
   2) washing, at least once, the separated epimerization-active solid with a solvent that can be the same or different from the solvent in which the ester to be epimerized was contacted,
   3) combining the washings with the separated solution of epimerized ester, and
   4) removing solvent to obtain the epimerized ester.

24. In a process for making calcipotriene, the steps of:
   a) acetylating an alcohol selected from XI and XII, wherein $R_1$ and $R_2$ are independently H or a silyl hydroxyl protecting group,

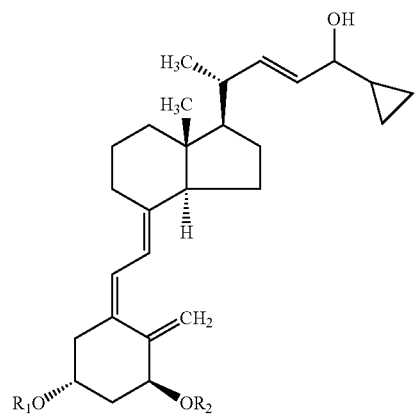

24 R

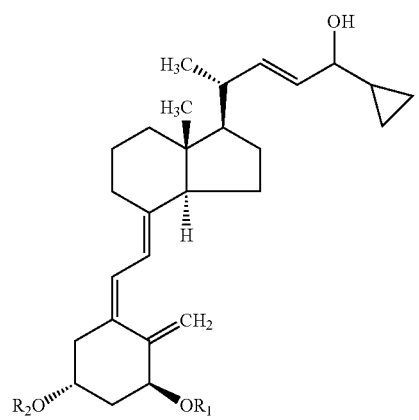

a) 24 S, b) 24 R b) contacting a solution of the acetate in a solvent selected from hexane, heptane, toluene, benzene, dichloromethane, ethyl acetate, and mixtures of these with an epimerization-active solid,
   c) separating the solution of epimerized ester from the epimerization-active solid,
   d) washing, at least once, the separated epimerization-active solid with a solvent that can be the same or different from the solvent in which the ester to be epimerized was contacted,
   e) combining the washings with the separated solution of epimerized ester, and
   f) removing solvent to obtain the epimerized ester.

* * * * *

UNITED STATES PATENT AND TRADEMARK OFFICE
CERTIFICATE OF CORRECTION

PATENT NO. : 7,205,420 B2  Page 1 of 6
APPLICATION NO. : 10/459073
DATED : April 17, 2007
INVENTOR(S) : Shapiro et al.

It is certified that error appears in the above-identified patent and that said Letters Patent is hereby corrected as shown below:

At column 2, lines 40-49, change

"
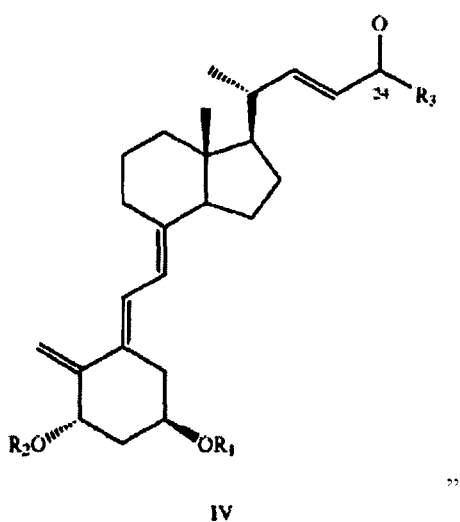
IV
"

to --
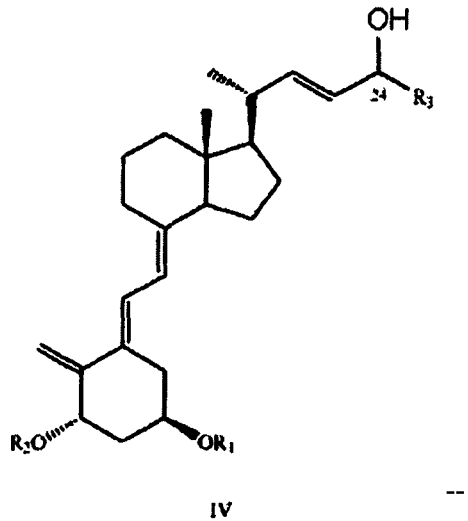
IV
--

CERTIFICATE OF CORRECTION (continued)
U.S. Pat. No. 7,205,420 B2

At column 5, line 64, change "empimerization" to -- epimerization --

At column 6, lines 25-45, change

"

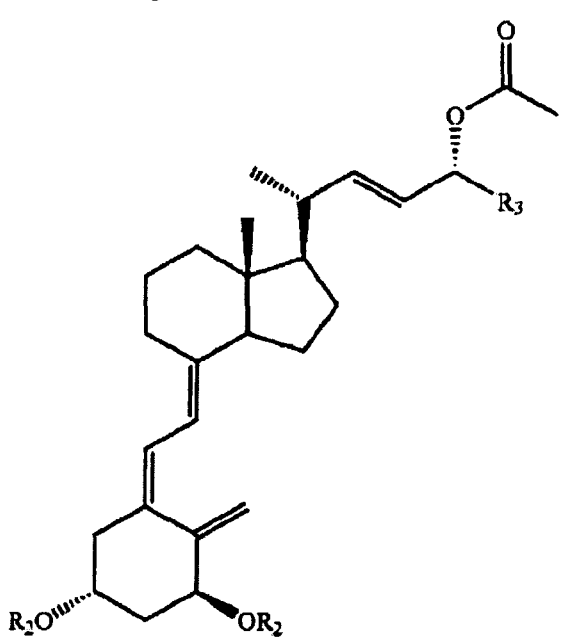

VI

"

to --

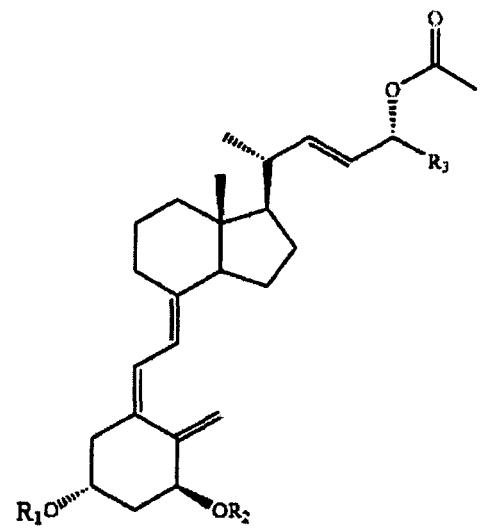

VI

--

At column 9, line 5, change "at only of" to -- at only one of --

At column 9, line 41, change "strating" to -- starting --

At column 10, line 59, change "chromatography" to -- chromatography --

At column 17, line 31, change "Preparation Calcipotriene" to -- Preparation of Calcipotriene --

At column 17, line 34, change "$R_3$ = cycloprpyl" to -- $R_3$ = cyclopropyl --

At column 18, line 39, change "alocihol" to -- alcohol --

At column 18, line 53, change "contacting >>" to -- contacting --

At column 19, lines 1-20, change

"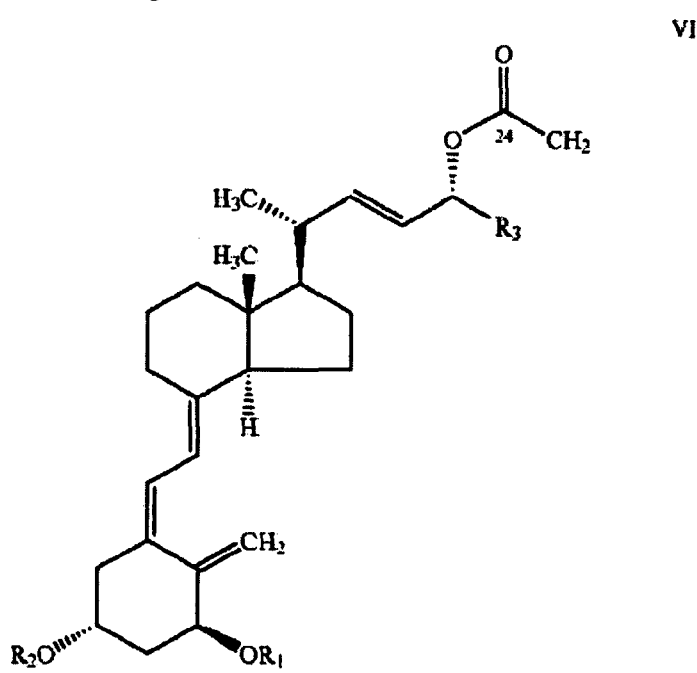"

to -- 
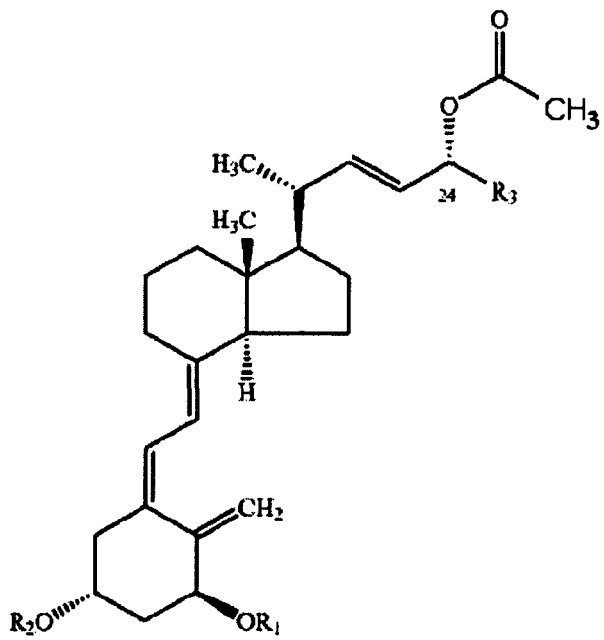
VI
At column 19, lines 21-40, change
"
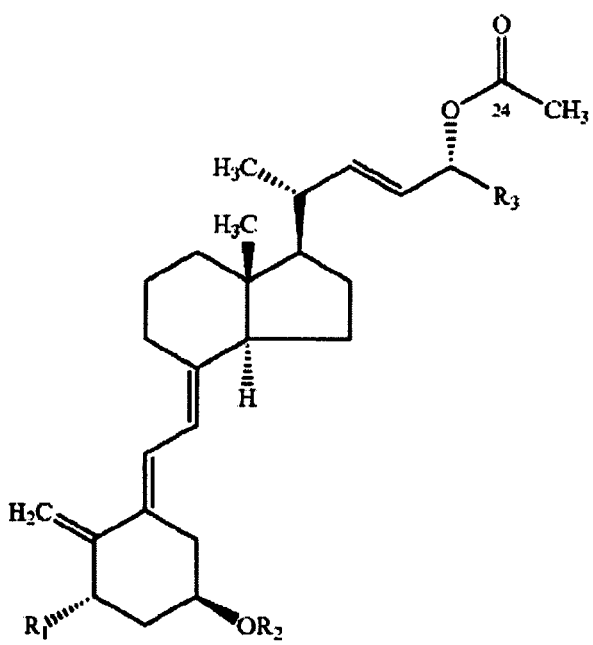
IX
"

to --
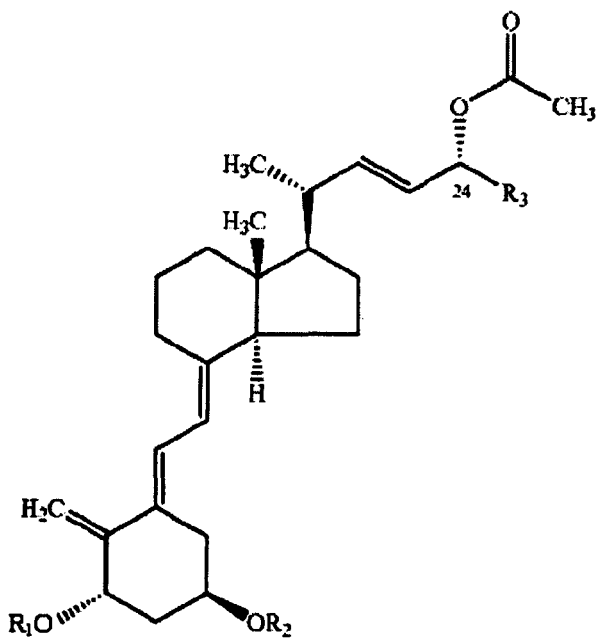
IX
At column 21, line 38, change "dihloromethane" to -- dichloromethane --
At column 22, lines 1-19, change
"
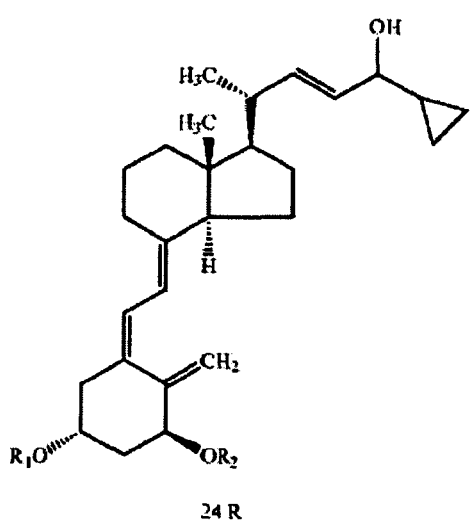
XI
24 R
"

CERTIFICATE OF CORRECTION (continued)
U.S. Pat. No. 7,205,420 B2 to -- 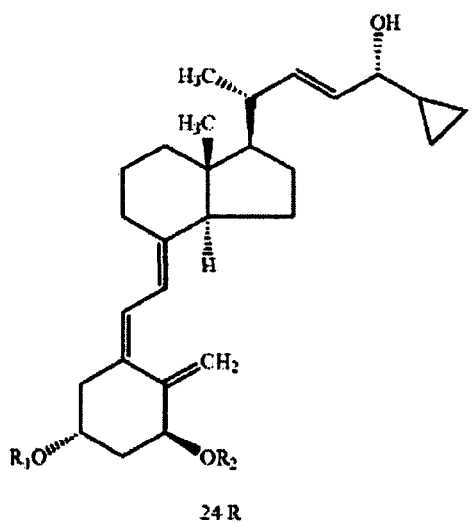 XI

24 R

--

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,205,420 B2 | Page 1 of 1 |
| APPLICATION NO. | : 10/459073 | |
| DATED | : April 17, 2007 | |
| INVENTOR(S) | : Shapiro et al. | |

It is certified that error appears in the above-identified patent and that said Letters Patent is hereby corrected as shown below:

At column 10, line 59, change "chromatigraphy" to -- chromatography --

Signed and Sealed this

Thirty-first Day of August, 2010

David J. Kappos
*Director of the United States Patent and Trademark Office*